(12) United States Patent
Kadokura

(10) Patent No.: US 8,021,304 B2
(45) Date of Patent: Sep. 20, 2011

(54) ULTRASONIC PROBE

(75) Inventor: Masahiko Kadokura, Sagamihara (JP)

(73) Assignee: Panasonic Corporation, Osaka (JP)

( * ) Notice: Subject to any disclaimer, the term of this patent is extended or adjusted under 35 U.S.C. 154(b) by 1056 days.

(21) Appl. No.: 10/554,458

(22) PCT Filed: May 19, 2004

(86) PCT No.: PCT/JP2004/007127
§ 371 (c)(1),
(2), (4) Date: Oct. 24, 2005

(87) PCT Pub. No.: WO2004/100796
PCT Pub. Date: Nov. 25, 2004

(65) Prior Publication Data
US 2006/0247528 A1    Nov. 2, 2006

(30) Foreign Application Priority Data
May 19, 2003    (JP) .................................. 2003-139697

(51) Int. Cl.
*A61B 8/14* (2006.01)
(52) U.S. Cl. .......................... 600/459; 600/462; 600/446
(58) Field of Classification Search .......... 600/437–472, 600/149
See application file for complete search history.

(56) References Cited

U.S. PATENT DOCUMENTS

| | | | | |
|---|---|---|---|---|
| 4,688,555 A * | 8/1987 | Wardle | ........................... | 600/149 |
| 4,895,158 A * | 1/1990 | Kawabuchi et al. | .......... | 600/463 |
| 4,913,158 A | 4/1990 | Kikuchi et al. | | |
| 5,048,529 A * | 9/1991 | Blumenthal | .................. | 600/446 |
| 5,255,684 A * | 10/1993 | Rello | ............................. | 600/463 |
| 5,450,851 A * | 9/1995 | Hancock | ........................ | 600/462 |
| 5,479,929 A * | 1/1996 | Cooper et al. | ................. | 600/459 |
| 5,494,040 A * | 2/1996 | Nakao et al. | .................. | 600/463 |
| 5,662,116 A * | 9/1997 | Kondo et al. | .................. | 600/462 |
| 5,667,476 A * | 9/1997 | Frassica et al. | ............... | 600/149 |
| 5,833,616 A * | 11/1998 | Gruner et al. | .................. | 600/462 |
| 5,938,551 A * | 8/1999 | Warner | ........................ | 474/111 |
| 6,569,100 B2 * | 5/2003 | Okawa et al. | ................. | 600/445 |
| 6,613,253 B1 * | 9/2003 | Negishi et al. | ............... | 264/40.1 |
| 6,709,397 B2 * | 3/2004 | Taylor | ........................... | 600/459 |
| 6,840,938 B1 * | 1/2005 | Morley et al. | ................. | 606/51 |
| 7,182,008 B2 * | 2/2007 | Negishi et al. | .................... | 83/15 |
| 2002/0062080 A1 * | 5/2002 | Okawa et al. | ................. | 600/459 |
| 2003/0073907 A1 * | 4/2003 | Taylor | ........................... | 600/459 |
| 2007/0016060 A1 * | 1/2007 | Hwang | ........................... | 600/459 |

FOREIGN PATENT DOCUMENTS

| | | |
|---|---|---|
| JP | 8-168490 | 7/1996 |
| JP | 10-174686 | 6/1998 |
| JP | 10-179588 | 7/1998 |
| JP | 2000-237986 | 9/2000 |
| JP | 2001-170053 | 6/2001 |
| JP | 2002-153464 | 5/2002 |
| WO | 92/07512 A1 | 5/1992 |

* cited by examiner

*Primary Examiner* — Sanjay Cattungal
(74) *Attorney, Agent, or Firm* — Pearne & Gordon LLP

(57) ABSTRACT

A technique for reducing the looseness of a wire and reducing the positional error of an ultrasonic transducer is disclosed. According to the technique, inside a tip portion 3 of an insertion portion 2, middle pulleys 11a, 11b are placed between pulleys 6, 7. The middle pulley 11a is attached to a slider portion 14, and the slider portion (and the middle pulley 11a) is supported slidably in the direction orthogonal to the rotation direction of the pulley 6 along a slider guide portion 15 formed at the tip portion, and the position of a sliding direction is supported so as to be able to be fixed at the tip portion by a screw 13.

7 Claims, 5 Drawing Sheets

ULTRASONIC PROBE

TECHNICAL FIELD

The present invention relates to an ultrasonic probe for inserting an ultrasonic transducer into a body cavity and emitting ultrasonic waves into an organism and then receiving an echo signal thereof, and more particularly relates to an ultrasonic probe that, in order to swing an ultrasonic transducer placed inside an insertion portion to be inserted into a body cavity, transmits a rotation of a motor, which is placed inside a grip portion held by an operator outside the body cavity, to the ultrasonic transducer.

BACKGROUND ART

As a conventional ultrasonic probe, for example, as described in the following patent documents 1, 2 and 3, a method of transmitting a rotation of a motor through a wire to an ultrasonic transducer is known. FIG. 8 shows a sectional view of the conventional ultrasonic probe. Inside a grip portion 1, a motor 5 and a pulley 102 linked to its rotation shaft are placed. Inside a tip portion 3 of an insertion portion 2, an ultrasonic transducer 4 and a pulley 7 linked to its rotation shaft 9 are placed. Then, an endless wire 8 is laid between the pulleys 102, 7, and the rotation of the motor 5 is transmitted to the rotation shaft 9 of the ultrasonic transducer 4.

Patent Document 1: Japanese Patent Application publication (H10-179588) (FIG. 3, Paragraph 0049)
Patent Document 2: Japanese Patent Application publication (H10-174686) (FIG. 1, Paragraph 0052)
Patent Document 3: Japanese Patent Application publication (2001-170053) (FIG. 2, Paragraph 0010)

However, in the foregoing conventional ultrasonic probe, the wire 8 is laid so as to be extended from the grip portion 1 to the tip portion 3 of the insertion portion 2, and it is relatively long. Thus, this has a problem that looseness of the wire 8 is generated, which causes a positional error of the ultrasonic transducer 4.

DISCLOSURE OF THE INVENTION

The present invention solves the foregoing conventional problems and has an object to provide an ultrasonic probe that can reduce the looseness of a wire and reduce the positional error of an ultrasonic transducer.

In order to attain the foregoing object, the present invention is configured such that an ultrasonic probe for transmitting a rotation of a motor, which is placed inside a grip portion in order to swing an ultrasonic transducer placed inside a tip portion of a longitudinal insertion portion, to the ultrasonic transducer, includes:

a rotation shaft linked to a rotation shaft of the motor so that a tip is extended inside the tip portion of the insertion portion;
a first pulley attached to a tip of the rotation shaft;
a second pulley attached to a swinging shaft of the ultrasonic transducer;
a middle pulley placed between the first and second pulleys;
a wire laid between the first and second pulleys and the middle pulley; and
a sliding mechanism for sliding the middle pulley and fixing to the tip portion so that the wire is not loosened.

With the foregoing configuration, the wire can be made shorter than the conventional example. Thus, the looseness of the wire can be reduced, thereby reducing the positional error of the ultrasonic transducer.

Also, this is configured such that the sliding mechanism has:

a slider portion to which the middle pulley is attached and which can be slid in a direction orthogonal to a rotation direction of the first pulley along a slider guide portion formed at the tip portion; and
a screw for fixing the slider portion to the tip portion.

With the foregoing configuration, the looseness of the wire can be reduced, thereby reducing the positional error of the ultrasonic transducer.

Also, this is configured such that the wire is made of a line material having both ends and has a block for fixing both of the ends of the line material, and the block is attached to the first pulley.

With the foregoing configuration, the wire can be easily laid between the first and second pulleys and the middle pulley.

BEST MODE FOR CARRYING OUT THE INVENTION

First Embodiment

Figure 1:
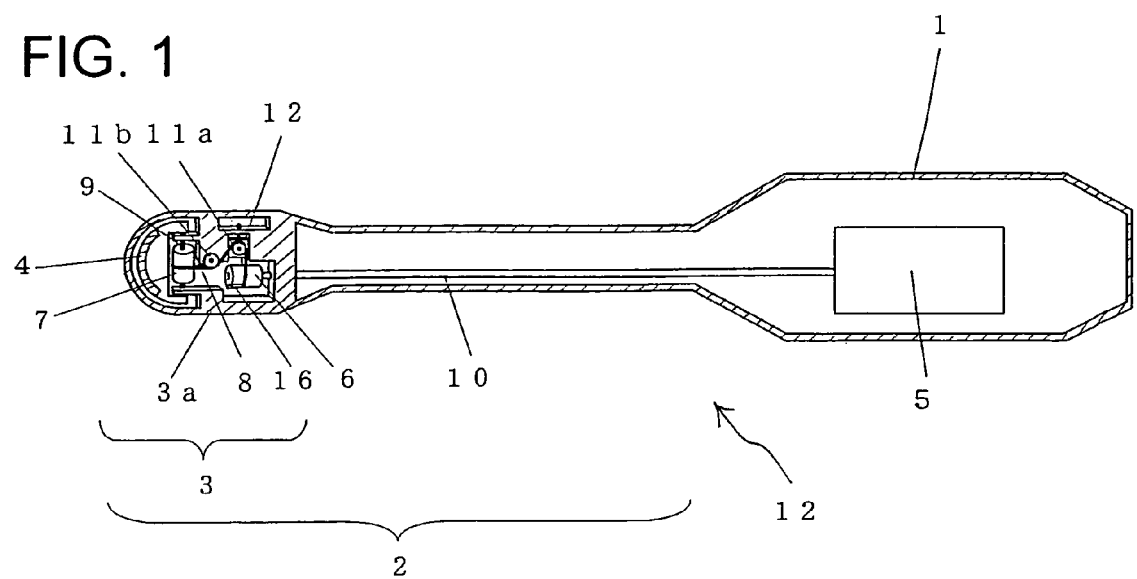
FIG. 1 is a sectional view of an ultrasonic probe in a first embodiment of the present invention.
Figure 2:
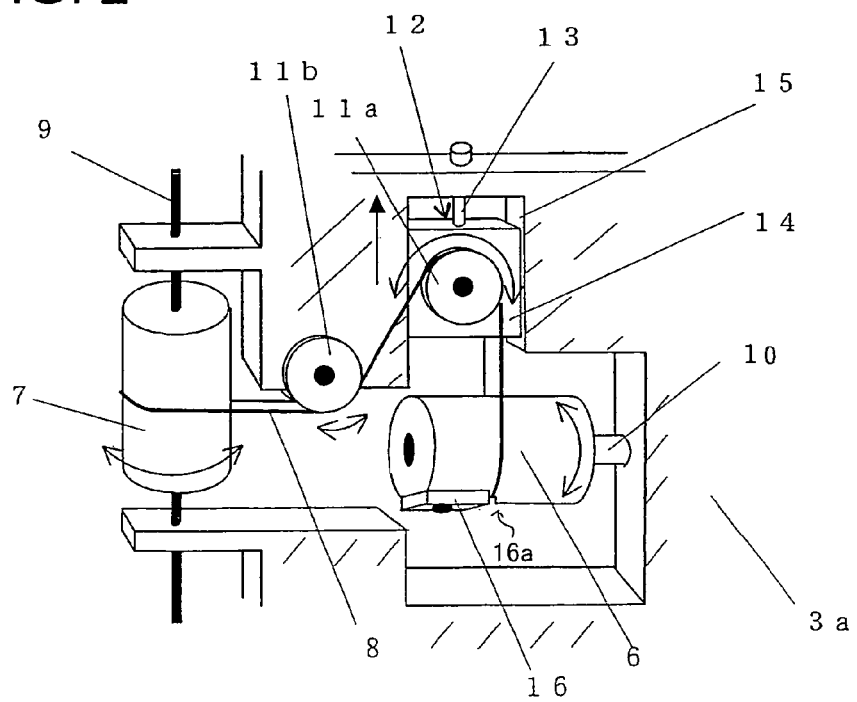
FIG. 2 is a sectional view that enlarges and shows a tip portion of FIG. 1.

Hereinbelow, with reference to the drawings, description will be given about embodiments to the present invention. An ultrasonic probe in the first embodiment of the present invention is shown in FIG. 1, FIG. 2, FIGS. 3A, 3B and 3C. At first, in those drawings, a motor 5 is placed inside a grip portion 1, and the motor 5 is configured such that a rotation shaft 10 is extended to a tip portion 3 of an insertion portion 2. Then, a pulley 6 as a first pulley is attached to the tip of the rotation shaft 10 of the motor 5. Around the circumference of the pulley 6, in such a way that a wire 8 does not fall away in a shaft direction, a part is flatly formed, and a plate portion 16 is attached onto its flat surface. A groove 16a for fastening the wire is formed in a circumferential direction between the circumference of the pulley 6 and the plate portion 16. An arc ultrasonic transducer 4 and a pulley 7 as a second pulley linked to its rotation shaft 9 are placed inside the tip portion 3 of the insertion portion 2. The axis direction of the pulley 6 on the motor 5 side and the axis direction of the rotation shaft 9 on the ultrasonic transducer 4 side are orthogonal.

Inside the tip portion 3 of the insertion portion 2, middle pulleys 11a, 11b are also placed between the pulleys 6, 7. The middle pulley 11a is attached to a slider portion 14, and the slider portion 14 (and the middle pulley 11a) is supported slidably in the direction orthogonal to the axis of the pulley 6 along a slider guide portion 15 formed in a base portion 3a of the tip portion 3, and the position of a sliding direction is supported so as to be able to be fixed at the base portion 3a by a screw 13. Those screw 13, slider portion 14 and slider guide portion 15 constitute a sliding mechanism 12 of the middle pulley 11a.

Figure 3A:
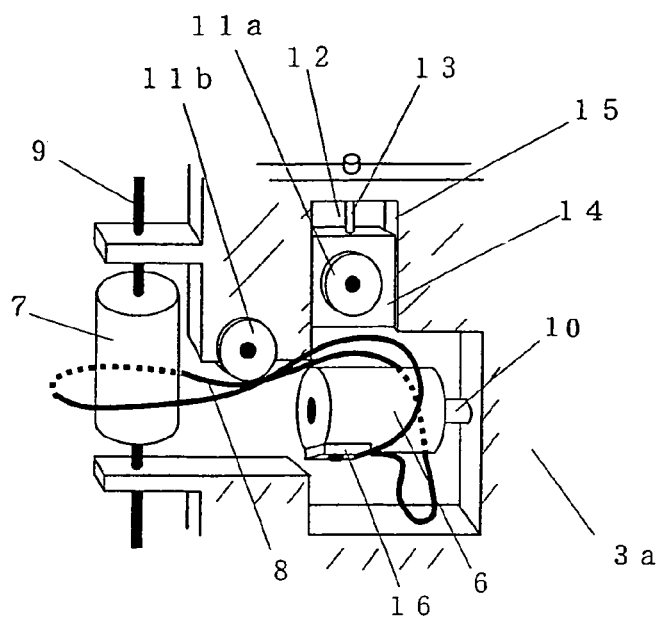
FIG. 3A is a sectional view of a situation where a wire at a tip portion of an ultrasonic probe in the first embodiment of the present invention is laid between first and second pulleys.
Figure 3B:
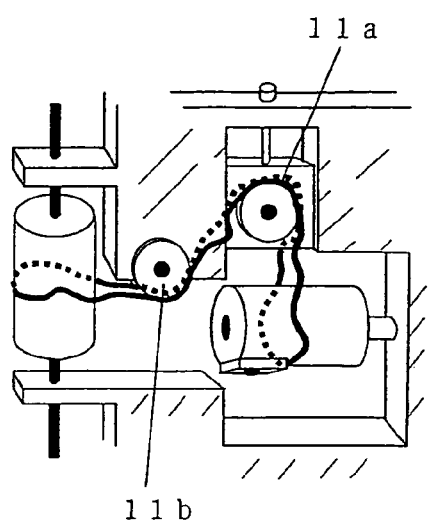
FIG. 3B is a sectional view of a situation where the wire at the tip portion of the ultrasonic probe in the first embodiment of the present invention is laid in a middle pulley.
Figure 3C:
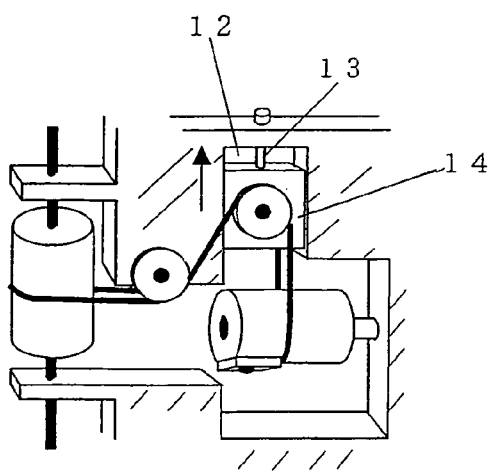
FIG. 3C is a sectional view of a situation where the wire at the tip portion of the ultrasonic probe in the first embodiment of the present invention is completely laid.

Then, the endless wire 8 is laid between the pulley 6, the middle pulleys 11a, 11b and the pulley 7. FIGS. 3A to 3C show the laying method of the wire 8. At first, as shown in FIG. 3A, in a situation where the slider portion 14 is moved to the looseness direction of the wire, the wire 8 is laid in the pulley 7 on the ultrasonic transducer 4 side, and it is fastened in the groove 16a (refer to FIG. 2) of the pulley 6 on the motor 5 side, and it is then laid between the middle pulleys 11a, 11b as shown in FIG. 3B. Next, as shown in FIG. 3C, the slider portion 14 is slid in the fastened direction of the wire and fixed by the screw 13. Thus, the sliding mechanism 12 can protect the looseness of the wire 8 by moving the middle pulley 11a, which is placed between the slider portion 14 and the slider portion 14 with the screw 13, to an arrow direction.

With regard to the ultrasonic probe configured as mentioned above, the operation thereof will be described below. In FIG. 1, outside a body cavity, an operator can hold the grip portion 1 and insert the insertion portion 2 into the body cavity. By using the motor 5, it is possible to perform the rotational motion on the pulley 6 set in the rotation shaft 10, and transmit the rotational motion of the pulley 6 through the middle pulleys 11a, 11b via the wire 8 to the pulley 7, and then perform the swinging motion around the rotation shaft 9 on the ultrasonic transducer 4.

Thus, the wire 8 can be made shorter than the conventional example. Also, in the sliding mechanism 12, since the slider portion 14 where the middle pulley 11a is set is fixed with the screw 13, the looseness of the wire 8 can be protected. Since the looseness of the wire 8 is decreased, the positional error of the ultrasonic transducer 4 can be reduced, thereby attaining the accurate positioning.

By the way, there may be a plurality of middle pulleys 11a, 11b as shown in the drawings. Also, this embodiment describes the case where the sliding mechanism 12 is placed in one of the two middle pulleys 11a, 11b. However, this is not limited thereto.

Second Embodiment

Figures 4A, 4B, 4C, 4D:
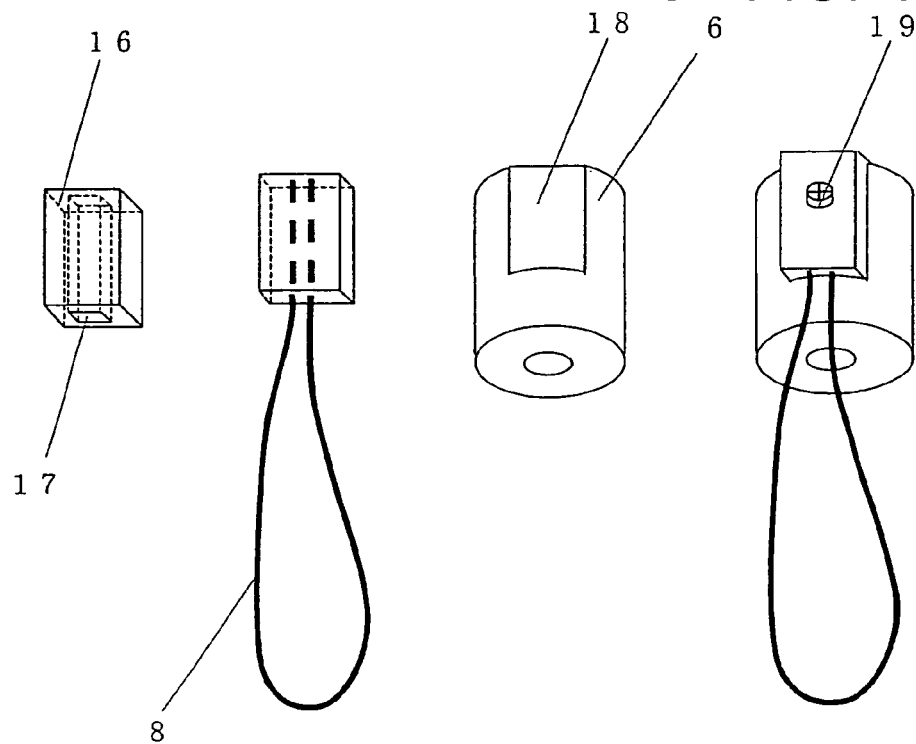
FIG. 4A is a configuration view showing a plate portion of an ultrasonic probe in a second embodiment of the present invention.
FIG. 4B is a configuration view showing a situation where a wire of the ultrasonic probe in the second embodiment of the present invention is fixed to the plate portion.
FIG. 4C is a configuration view showing a first pulley of the ultrasonic probe in the second embodiment of the present invention.
FIG. 4D is a configuration view showing a situation where the plate portion of the ultrasonic probe in the second embodiment of the present invention is fixed to the first pulley.

The ultrasonic probe in the second embodiment will be described below with reference to FIGS. 4A to 4D. At first, as shown in FIG. 4A, an attaching hole 17 of the wire 8 is formed in the plate portion 16. Then, as shown in FIG. 4B, both ends of one wire 8 that has both the ends (is not endless) is inserted into this attaching hole 17, and the plate portion 16 is crushed, thereby fixing both of the ends of the wire 8. On a part of the circumference of the pulley 6, as shown in FIG. 4C, a flat surface 18 is formed. Then, as shown in FIG. 4D, the plate portion 16 is attached onto this flat surface 18 with a screw 19. According to this second embodiment, after the wire 8 that is not endless is made endless by the plate portion 16, it is easily attached to the pulley 6.

Figure 5:
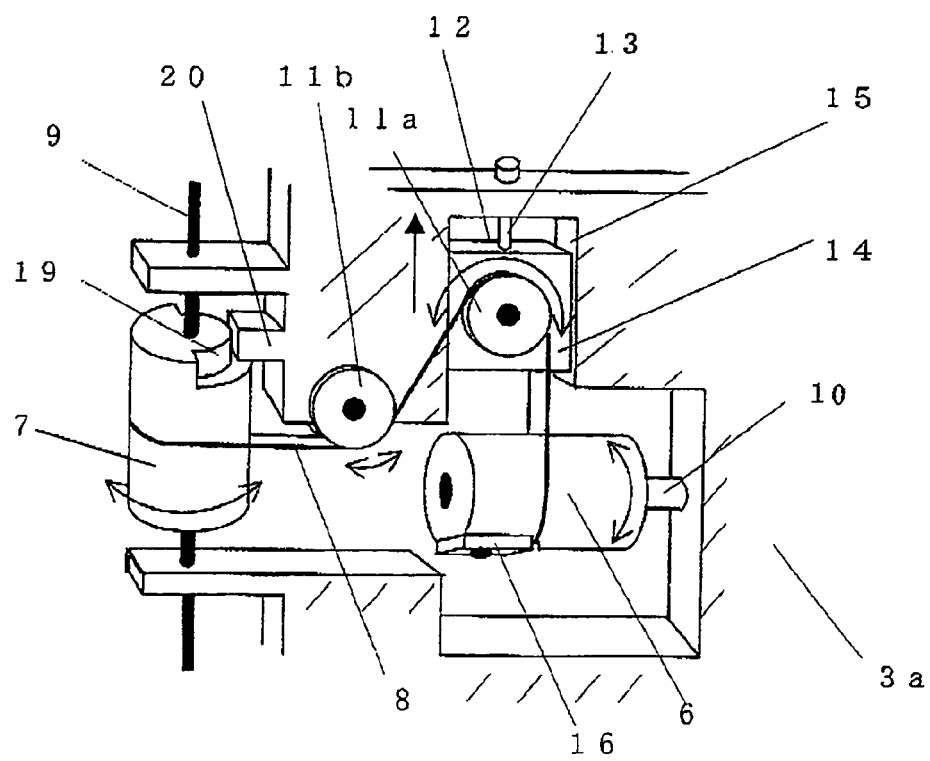
FIG. 5 is a sectional view of the ultrasonic probe in the first embodiment of the present invention.

By the way, in FIG. 5, a notch portion 19 may be formed in the shape of a circle around the second pulley 7, oppositely to a protrusion 20 placed on the base portion 3a. When the ultrasonic transducer 4 receives the impact caused by a drop and the like, it is rotated around the rotation shaft 10, and the protrusion 20 and the end surface of the notch portion 19 are hit. Correspondingly, this can protect the ultrasonic transducer 4 from being hit against the base portion 3a and protect the ultrasonic transducer from being damaged.

Figure 6:
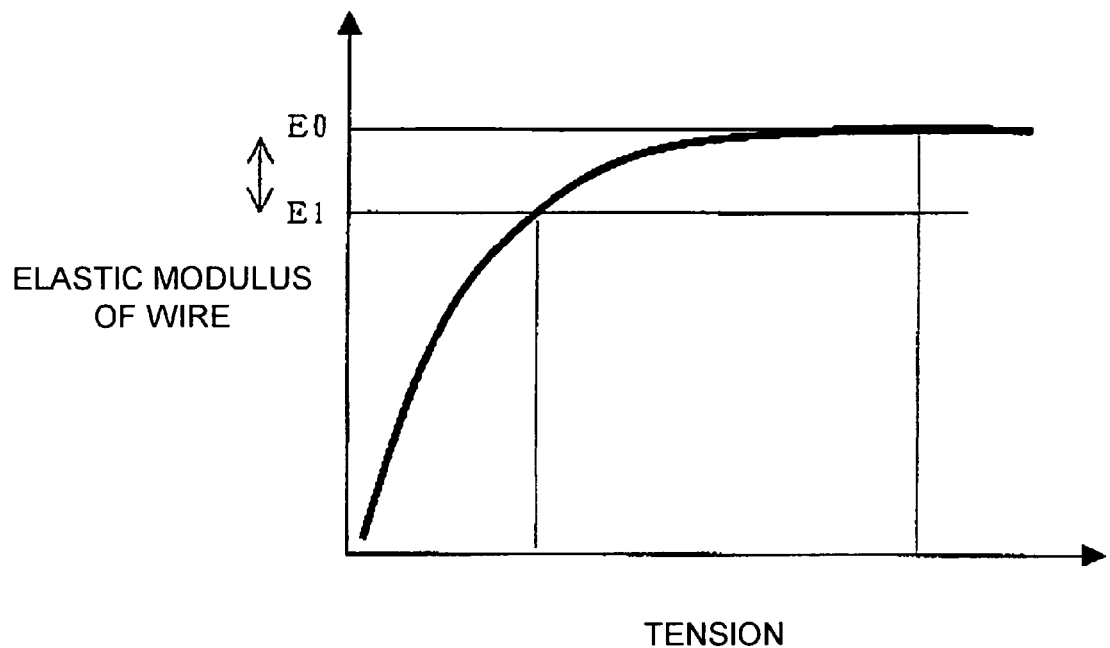
FIG. 6 is a graph with regard to a wire tension in the first embodiment of the present invention.

By the way, in order to protect the looseness of the wire 8, in the graph of a tension of the wire and an elastic coefficient of the wire in FIG. 6, the tension applied to the wire 8 is desired to be in the range of the tension where an elastic constant E1 is within 30% with respect to an elastic constant E0 where the elastic coefficient of the wire is constant for the tension. This is because as the elastic modulus of wire is lower, the inertia of the ultrasonic transducer 4 when it is swung causes the wire to be elastically extended, which results in the larger position displacement.

Figure 7:
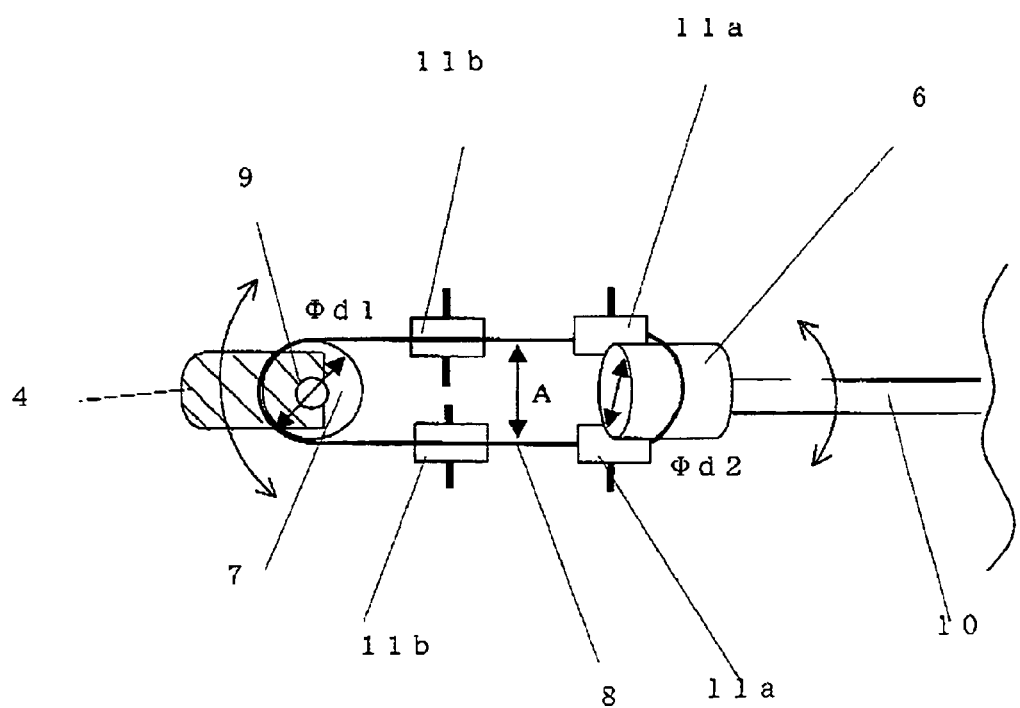
FIG. 7 is a sectional view (top view) of the ultrasonic probe in the first embodiment of the present invention.
Figure 8:
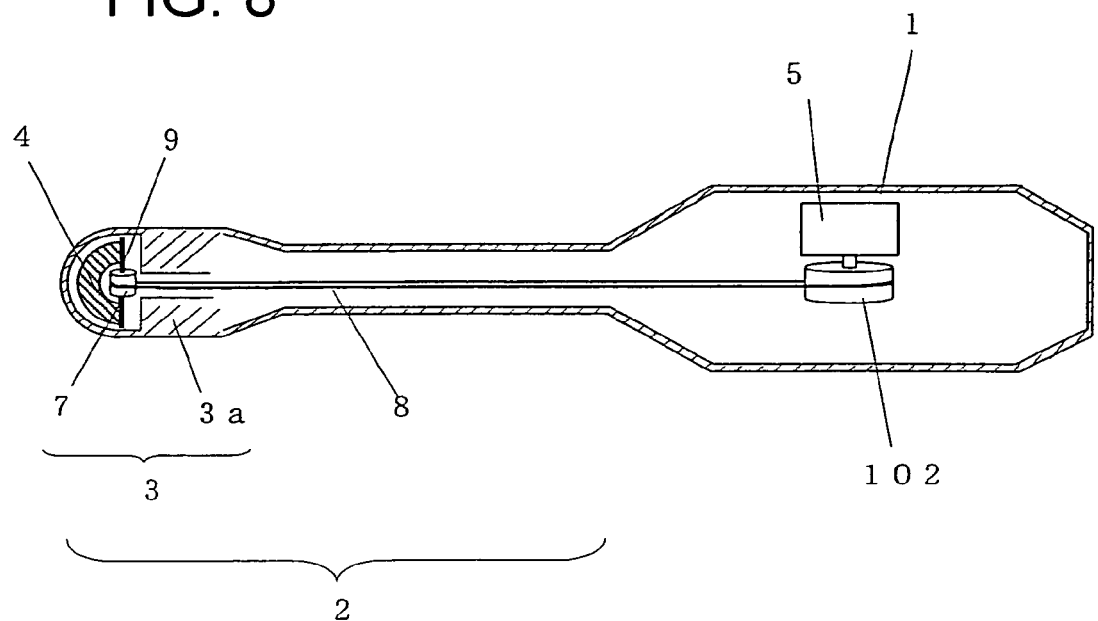
FIG. 8 is a sectional view of a conventional ultrasonic probe.

By the way, in FIG. 7, in a diameter $\Phi d1$ of the first pulley, a diameter $\Phi d2$ of the second pulley and a distance A between the positions for which the wires of the pulleys where the middle pulleys 11a, 11b are opposite to each other are set, $\Phi d1 = \Phi d2 = A$ is desired. This is intended such that the wire is set vertically for the rotation axis of any pulley. Consequently, the force that is obliquely applied to the rotation axis of the pulley of the wire can be avoided, thereby reducing the sideslip on the pulley of the wire.

INDUSTRIAL APPLICABILITY

As mentioned above, according to the present invention, the wire can be made shorter than the conventional example. Thus, the looseness of the wire can be reduced, and the positional error of the ultrasonic transducer can be reduced. Hence, the present invention is useful for the field of the ultrasonic probe that is inserted into the body cavity.

The invention claimed is:

1. An ultrasonic probe comprising:
   a motor positioned inside a grip portion, wherein the motor is adapted to transmit rotation to an ultrasonic transducer to swing the ultrasonic transducer, further wherein the ultrasonic transducer is positioned within a tip portion of a longitudinal insertion portion;
   a rotation shaft linked to a rotation shaft of said motor so that a tip is extended inside the tip portion of said insertion portion;
   a first pulley attached to said tip of said rotation shaft;
   a second pulley attached to a swinging shaft of said ultrasonic transducer;
   a middle pulley placed between said first and second pulleys;
   a wire laid between said first and second pulleys and said middle pulley; and
   a sliding mechanism for supporting said middle pulley in such a manner that said middle pulley is slidable in a direction toward and away from said first pulley and in a direction parallel to the longitudinal axis of the swinging shaft to reduce looseness of the wire before operation and the middle pulley can be positioned so that a distance between said middle pulley and said first pulley is kept constant during operation, and said middle pulley is not movable in a longitudinal direction of said longitudinal insertion portion.

2. The ultrasonic probe according to claim 1, wherein said sliding mechanism includes:
   a slider portion to which said middle pulley is attached and which can be slid in a direction orthogonal to a rotation direction of said first pulley along a slider guide portion formed at said tip portion; and
   a screw for fixing said slider portion to said tip portion.

3. The ultrasonic probe according to claim 1, wherein said wire is made of a line material having both ends and has a block for fixing both of the ends of said line material, and said block is attached to said first pulley.

4. The ultrasonic probe according to claim 1, wherein said wire is confined within said tip portion.

5. The ultrasonic probe according to claim 1, wherein said middle pulley is slidable in a slide guide formed integrally in the tip portion.

6. An ultrasonic probe comprising:
   a motor positioned inside a grip portion, wherein the motor is adapted to transmit rotation to an ultrasonic transducer to swing the ultrasonic transducer, further wherein the ultrasonic transducer is positioned within a tip portion of a longitudinal insertion portion;
   a rotation shaft having an axis of rotation linked to a rotation shaft of said motor so that a tip is extended inside the tip portion of said insertion portion;
   a first pulley attached to said tip of said rotation shaft, wherein said pulley rotates about said axis of rotation of said rotation shaft;
   a second pulley attached to a swinging shaft of said ultrasonic transducer, wherein the swinging shaft is formed substantially coaxially with the second pulley;
   a middle pulley placed between said first and second pulleys;
   a wire laid between said first and second pulleys and said middle pulley; and
   a sliding mechanism for sliding said middle pulley in a direction parallel to a longitudinal axis of the swinging shaft without moving said middle pulley in a longitudinal direction of said insertion portion so that said wire is not loosened.

7. An ultrasonic probe comprising:
   a motor positioned inside a grip portion, wherein the motor is adapted to transmit rotation to an ultrasonic transducer to swing the ultrasonic transducer, further wherein the ultrasonic transducer is positioned within a tip portion of a longitudinal insertion portion;
   a rotation shaft having an axis of rotation linked to a rotation shaft of said motor so that a tip is extended inside the tip portion of said insertion portion;
   a first pulley attached to said tip of said rotation shaft, wherein said pulley rotates about said axis of rotation of said rotation shaft;
   a second pulley attached to a swinging shaft of said ultrasonic transducer, wherein the swinging shaft is formed substantially coaxially with the second pulley;
   a middle pulley placed between said first and second pulleys;
   a wire laid between said first and second pulleys and said middle pulley; and
   a sliding mechanism for sliding said middle pulley in a direction parallel to the swinging shaft without moving said middle pulley in a longitudinal direction of said insertion portion to adjust tension of said wire.

* * * * *